United States Patent
Takemoto et al.

(10) Patent No.: US 8,475,041 B2
(45) Date of Patent: Jul. 2, 2013

(54) X-RAY DIAGNOSTIC APPARATUS

(75) Inventors: Hisato Takemoto, Nasushiobara (JP); Ryuji Zaiki, Utsunomiya (JP); Takuya Sakaguchi, Shioya-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 715 days.

(21) Appl. No.: 12/647,220

(22) Filed: Dec. 24, 2009

(65) Prior Publication Data

US 2010/0166152 A1    Jul. 1, 2010

(30) Foreign Application Priority Data

Dec. 25, 2008  (JP) .................................. 2008-331045
Dec. 21, 2009  (JP) .................................. 2009-289138

(51) Int. Cl.
*H05G 1/02*    (2006.01)
*A61B 6/00*    (2006.01)

(52) U.S. Cl.
CPC .................................. *A61B 6/4476* (2013.01)
USPC ...................................................... 378/197

(58) Field of Classification Search
CPC .................................................. A61B 6/4476
USPC ................. 378/114, 115, 117, 102, 197, 208, 378/209
See application file for complete search history.

(56) References Cited

U.S. PATENT DOCUMENTS

| 6,334,708 | B1 | 1/2002 | Kosugi |
| 7,020,510 | B2 | 3/2006 | Suurmond et al. |
| 7,298,824 | B2 * | 11/2007 | Watanabe ..................... 378/114 |
| 2006/0257006 | A1 * | 11/2006 | Bredno et al. ................ 382/128 |

FOREIGN PATENT DOCUMENTS

| CN | 1406117 A | 3/2003 |
| CN | 101028194 A | 9/2007 |
| JP | 2000-197621 | 7/2000 |

OTHER PUBLICATIONS

Office Action issued on Jun. 29, 2011 in the corresponding Chinese Application No. 200910262661.0 (with English Translation).

* cited by examiner

*Primary Examiner* — Irakli Kiknadze
(74) *Attorney, Agent, or Firm* — Oblon, Spivak, McClelland, Maier & Neustadt, L.L.P.

(57) ABSTRACT

An X-ray diagnostic apparatus includes imaging means including an X-ray application unit which applies X-rays to a subject and an X-ray detection unit which detects the X-rays applied from the X-ray application unit to pick up a medical image, path calculating means for obtaining a path of an imaging position for the subject on the basis of a map image, a storage unit which stores the path, imaging system moving means for movably supporting the imaging means to capture the imaging position in an imaging field and movement control means for moving the imaging system moving means to successively move the imaging position along the path.

16 Claims, 15 Drawing Sheets

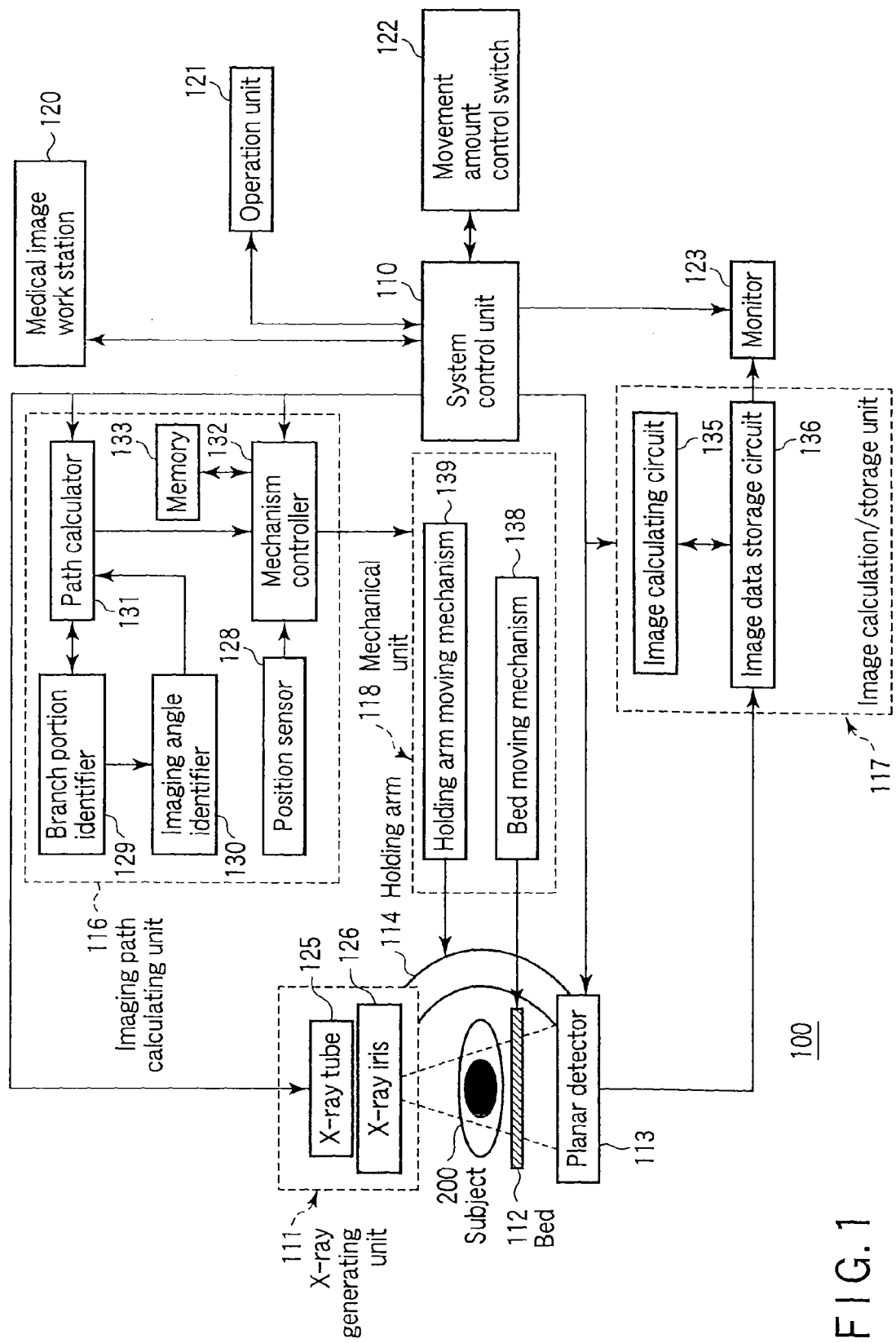
F I G. 1

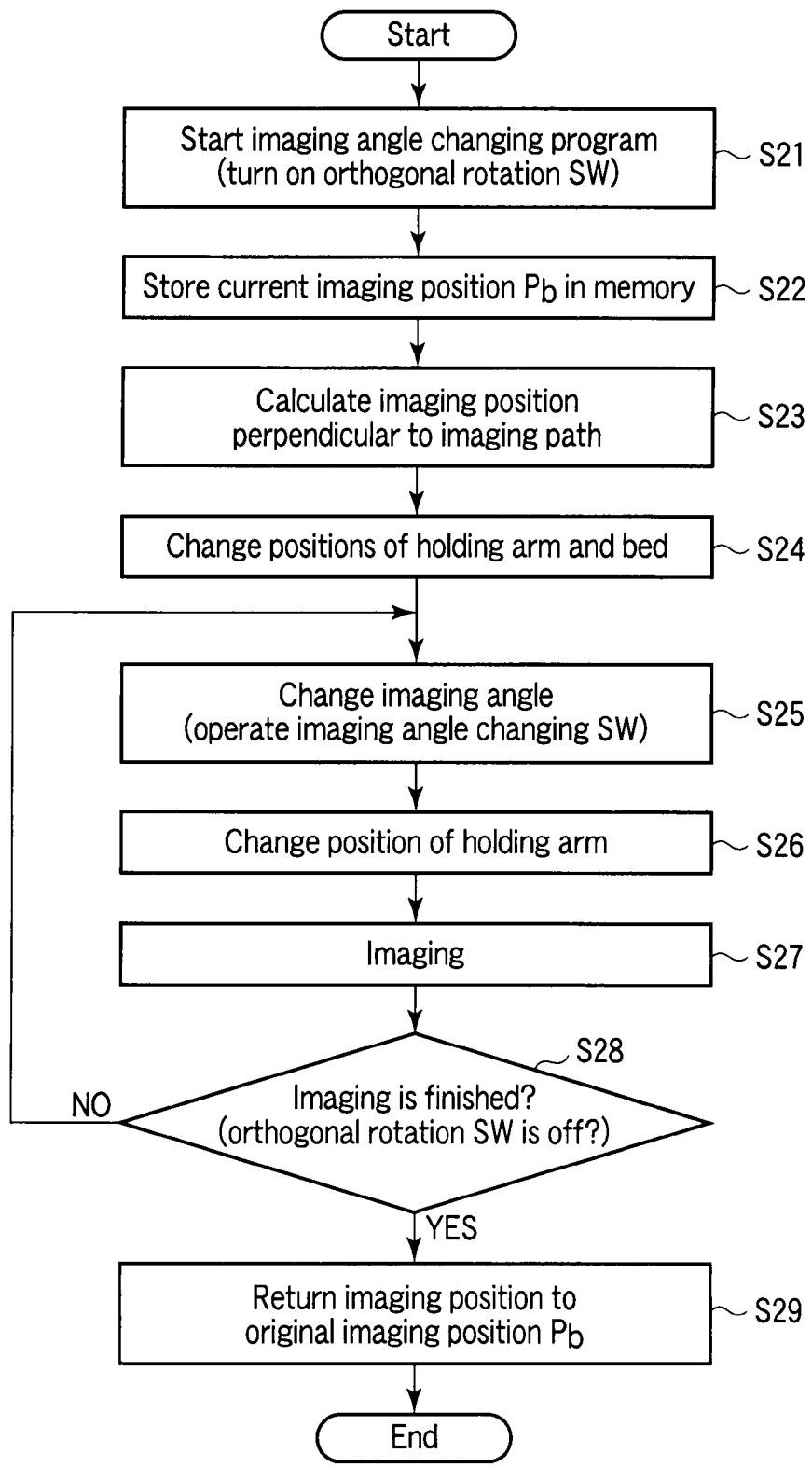
F I G. 6

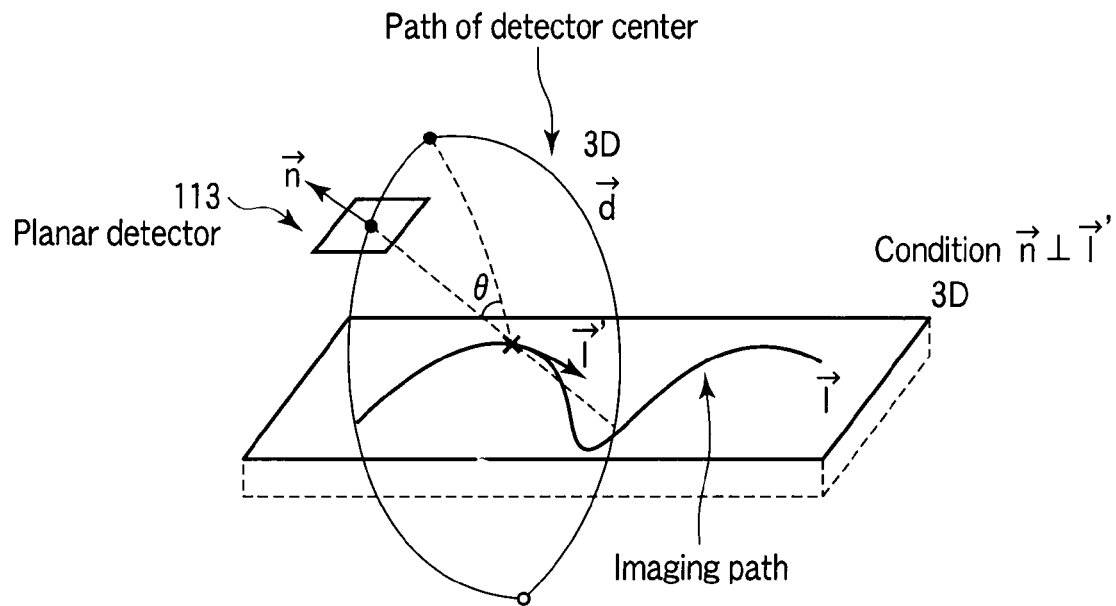
F I G. 7A
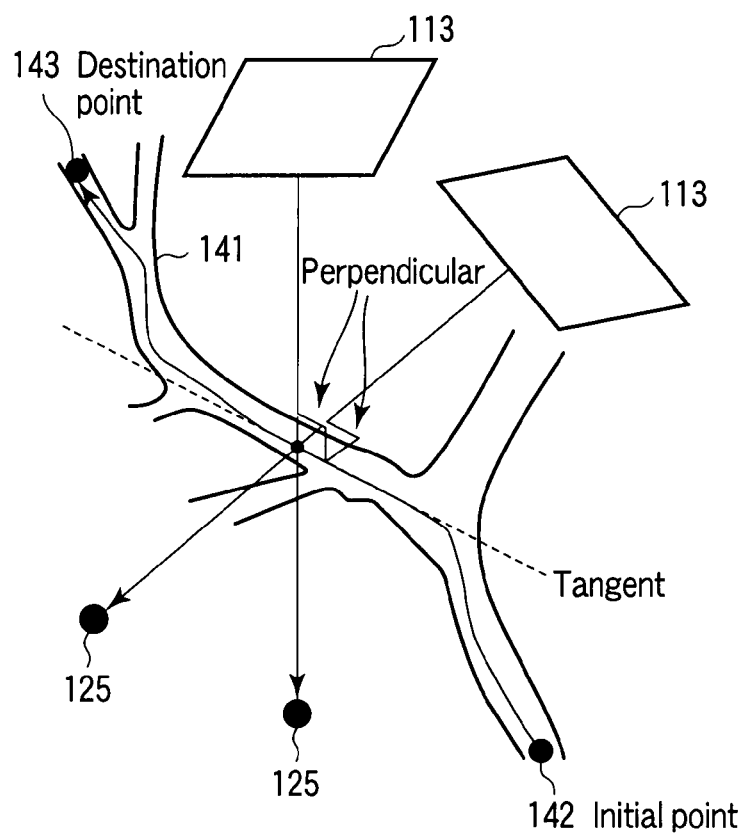
F I G. 7B

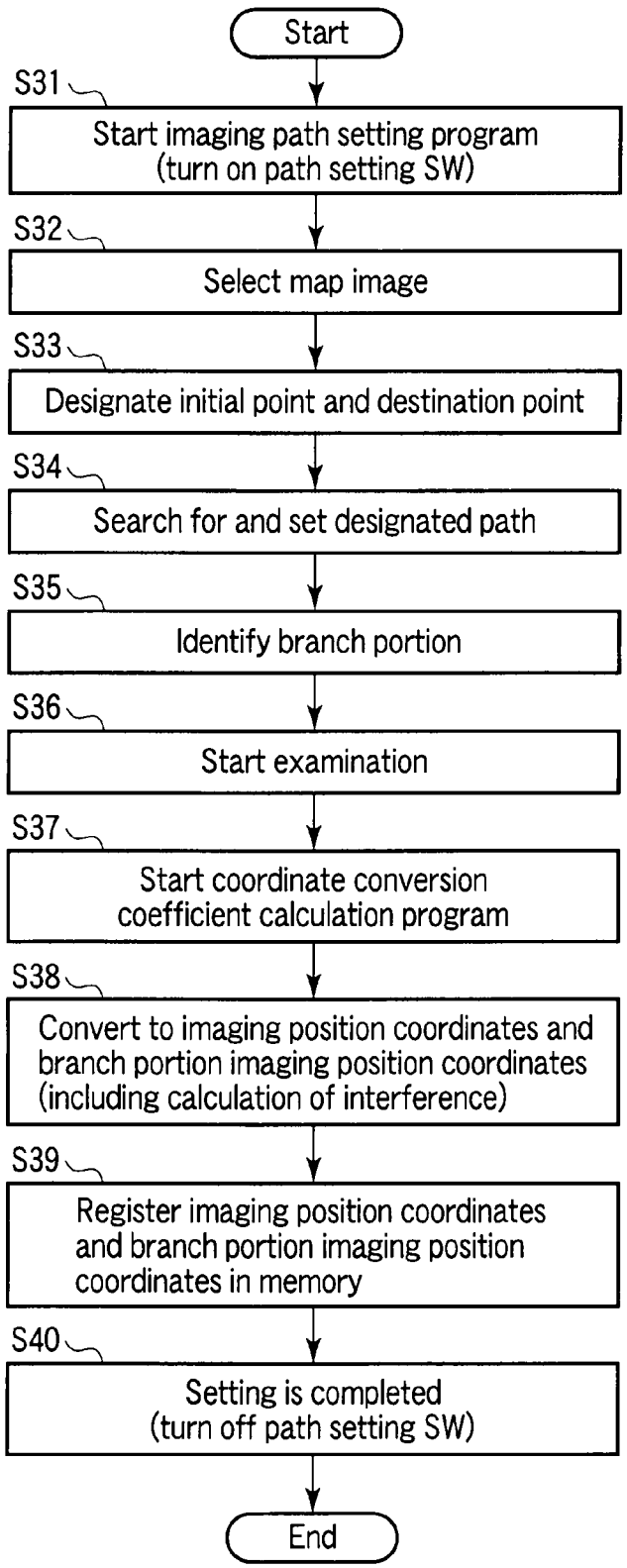
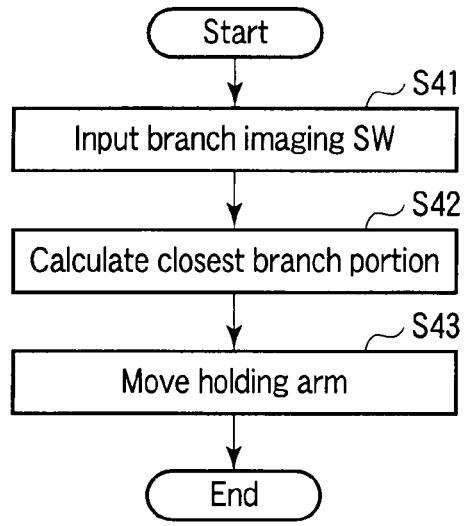
FIG. 8A
FIG. 8B

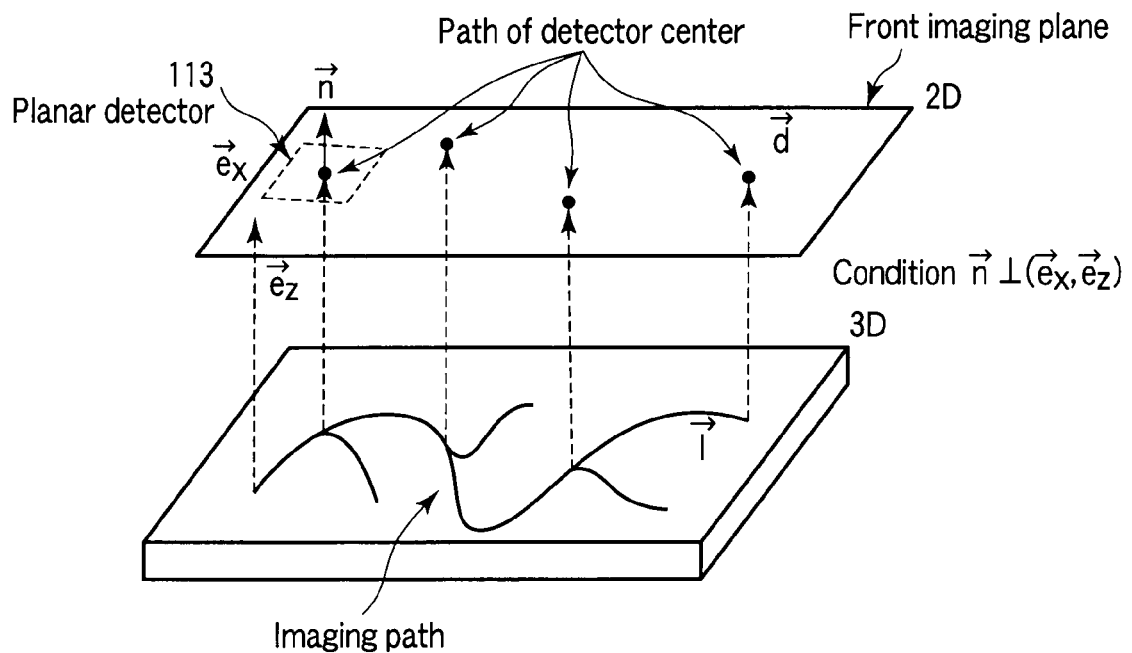
F I G. 9A
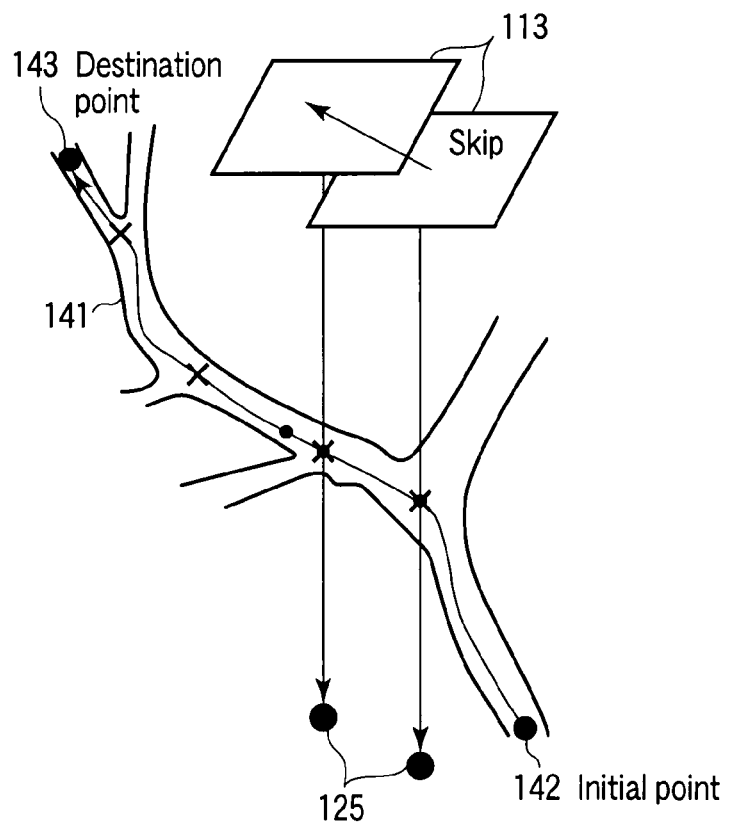
F I G. 9B

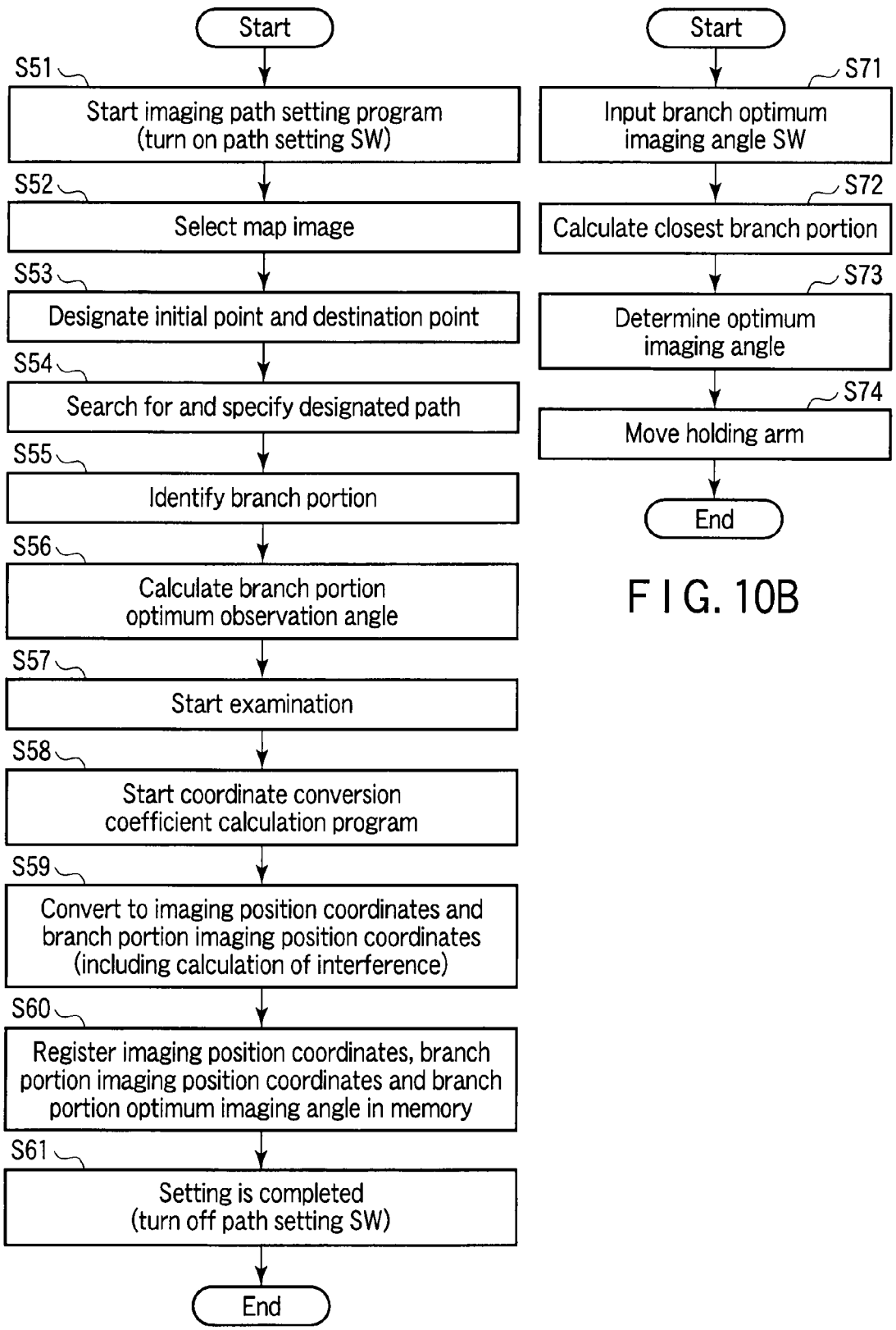

X-RAY DIAGNOSTIC APPARATUS

CROSS-REFERENCE TO RELATED APPLICATIONS

This application is based upon and claims the benefit of priority from prior Japanese Patent Applications No. 2008-331045, filed Dec. 25, 2008; and No. 2009-289138, filed Dec. 21, 2009, the entire contents of both of which are incorporated herein by reference.

BACKGROUND OF THE INVENTION

1. Field of the Invention

The present invention relates to an X-ray diagnostic apparatus. More particularly, the present invention relates to drawing of a wire route projected line for an intravascular treatment, especially for passage through complete obstruction, and also relates to an improvement in a method of determining an observation direction in an intravascular treatment.

2. Description of the Related Art

Recently, doctors rely on images of the inside of a body taken by an X-ray diagnostic apparatus to perform a catheterization procedure. During the catheterization procedure, the doctor may change imaging positions in accordance with the movement of a catheter, and change to an imaging position at which a vascular branch portion, if any, is easily viewed and then make an observation. A common way to change the imaging positions is to individually manipulate a top plate position and an arm position, which is, however, troublesome.

In the meantime, there is a conventional method known as autopositioning wherein frequently used imaging positions are preset (e.g., see Jpn. Pat. Appln. KOKAI Publication No. 2000-197621). In addition, the imaging positions include the position of a holding arm and the position of a bed where the center of a beam passes through imaging position coordinates.

However, in the technique described in Jpn. Pat. Appln. KOKAI Publication No. 2000-197621, a plurality of imaging positions are independently preset in a discrete manner. Therefore, for example, along the movement of an imaging position from an imaging position (1) to an imaging position (2), there is not always a position at which an image should be taken. Moreover, an imaging time cannot be designated at a middle position. That is, it is difficult to obtain a motion which is necessary during the movement of the catheter and which captures, as serial imaging fields, a path where the catheter would move. Moreover, the imaging time cannot be freely changed at every imaging position. Thus, this technique remains at an autopositioning function that only provides the imaging positions as inconsecutive points.

BRIEF SUMMARY OF THE INVENTION

It is an object of the present invention to provide an X-ray diagnostic apparatus capable of successively changing the imaging position along desired imaging positions by simply operating and reducing the time of a procedure.

According to an aspect of the present invention, there is provided an X-ray diagnostic apparatus comprising imaging means including an X-ray application unit which applies X-rays to a subject and an X-ray detection unit which detects the X-rays applied from the X-ray application unit to pick up a medical image, path calculating means for obtaining a path of an imaging position for the subject on the basis of a map image, a storage unit which stores the path, imaging system moving means for movably supporting the imaging means to capture the imaging position in an imaging field and movement control means for moving the imaging system moving means to successively move the imaging position along the path.

Additional objects and advantages of the invention, will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the configuration of an X-ray diagnostic apparatus according to a first embodiment of the present invention;

FIG. 6 is a flowchart for the explanation of processing performed under the control of a system control unit 110 in an X-ray diagnostic apparatus according to a second embodiment of the present invention;

FIG. 7A is a diagram showing the relation between an imaging path l and a movement path d of the center of a planar detector 113, in the second embodiment;

FIG. 7B is a diagram for the explanation of an initial point and a destination point on a vascular map image, in the second embodiment;

FIG. 8A is a flowchart for the explanation of processing performed under the control of a system control unit 110 in an X-ray diagnostic apparatus according to a third embodiment;

FIG. 8B is a flowchart for the explanation of processing performed under the control of the system control unit 110 in the X-ray diagnostic apparatus according to the third embodiment;

FIG. 9A is a diagram showing the relation between an imaging path l and a movement path d of the center of a planar detector 113, in the third embodiment;

FIG. 9B is a diagram for the explanation of an initial point and a destination point on a vascular map image, in the third embodiment;

FIG. 10A is a flowchart for the explanation of processing performed under the control of a system control unit 110 in an X-ray diagnostic apparatus according to a fourth embodiment;

FIG. 10B is a flowchart for the explanation of processing performed under the control of the system control unit 110 in the X-ray diagnostic apparatus according to the fourth embodiment;

DETAILED DESCRIPTION OF THE INVENTION

Figures 2A, 2B:
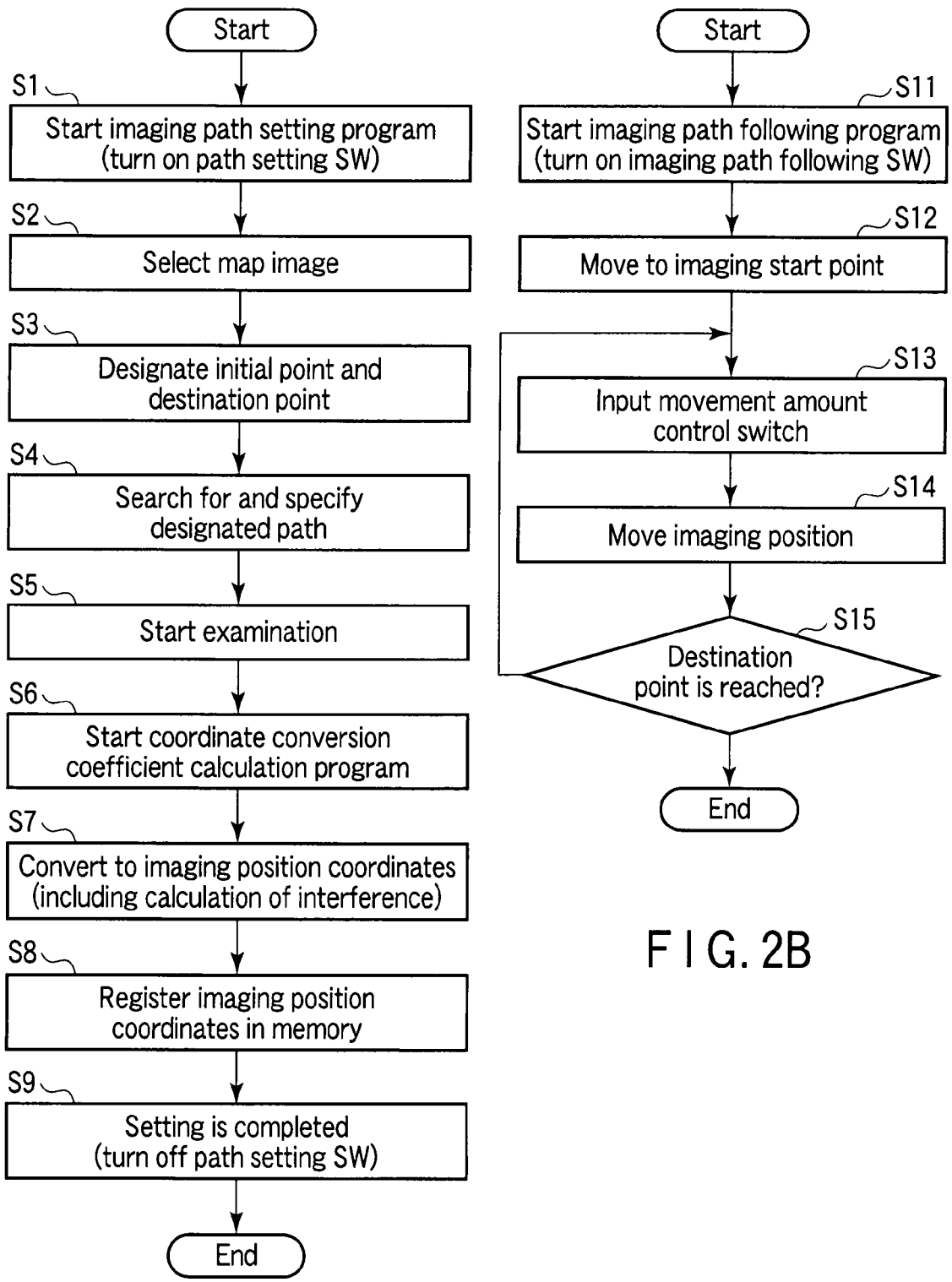
FIG. 2A is a flowchart for the explanation of processing performed under the control of a system control unit 110 in the X-ray diagnostic apparatus 100 according to the first embodiment.
FIG. 2B is a flowchart for the explanation of the movement of an imaging position enabled by using an imaging position movement amount control switch 122.

Hereinafter, preferred embodiments of an X-ray diagnostic apparatus according to the present invention will be described with reference to the drawings.

(First Embodiment)

According to a function described in a first embodiment, an imaging position movement amount control switch is used to allow a holding arm to control its forward movement, stop, backward movement and the speed of the movements so that imaging positions trace a preset route.

FIG. 1 is a block diagram showing the configuration of an X-ray diagnostic apparatus according to the first embodiment of the present invention.

In FIG. 1, an X-ray diagnostic apparatus 100 in the present embodiment comprises a system control unit 110 which has control over the whole X-ray diagnostic apparatus, an X-ray generating unit 111, a bed (top plate) 112 on which a subject 200 is mounted, a planar detector 113 for detecting X rays via the subject 200, a holding arm 114, an imaging path calculating unit 116, an image calculation/storage unit 117, a mechanical unit 118 for moving the bed 112 and the holding arm 114, a medical image work station 120, an operation unit 121, a movement amount control switch 122 and a monitor 123.

The X-ray generating unit 111 includes an X-ray tube 125 and an X-ray iris 126. The holding arm 114 is C-shaped so that the X-ray generating unit 111 and the planar detector 113 are arranged face to face with each other. The holding arm 114 is configured by one arm which is movable in the axial direction of the subject 200.

Furthermore, the imaging path calculating unit 116 includes a position sensor 128 for detecting an imaging path (passage) passing through blood vessels, a branch portion identifier 129, an imaging angle identifier 130, a path calculator 131, a mechanism controller 132 and a memory 133.

The image calculation/storage unit 117 includes an image calculating circuit 135 and an image data storage circuit 136. Image data stored in the image data storage circuit 136 is displayed as an image on the monitor 123. An operator operates the operation unit 121 while checking the image or the like displayed on the monitor 123, thereby enabling an X-ray diagnostic treatment.

The mechanical unit 118 includes a bed moving mechanism 138 and a holding arm moving mechanism 139. The bed moving mechanism 138 moves the position of the bed 112. The holding arm moving mechanism 139 moves the holding arm 114 which arranges the X-ray generating unit 111 and the planar detector 113 face to face with each other.

The operation unit 121 includes various operation switches for a user to actually operate a catheter or the like. The movement amount control switch 122 controls various moving mechanisms, and is configured by, for example, a foot switch.

In the X-ray diagnostic apparatus 100 having such a configuration, processing performed under the control of the system control unit 110 is described with reference to a flowchart in FIG. 2A.

When this sequence is started, an unshown path setting switch in the operation unit 121 is first operated in accordance with a user instruction in step S1 so that an imaging path setting program is started. Then, in step S2, in order to designate an imaging path which represents a designated path in a system-owned coordinate system, images stored in the medical image work station 120 are displayed on the monitor 123. From these images, the user selects a map image by use of an input device (not shown) of the operation unit 121. In this case, an image in which blood vessels are visualized, such as a computed topography (CT) image taken in the past, is selected as the map image.

Then, the medical image work station 120 creates a vascular map image from the selected map image in accordance with a user instruction, and the vascular map image is displayed on the monitor 123.

Figure 3A:
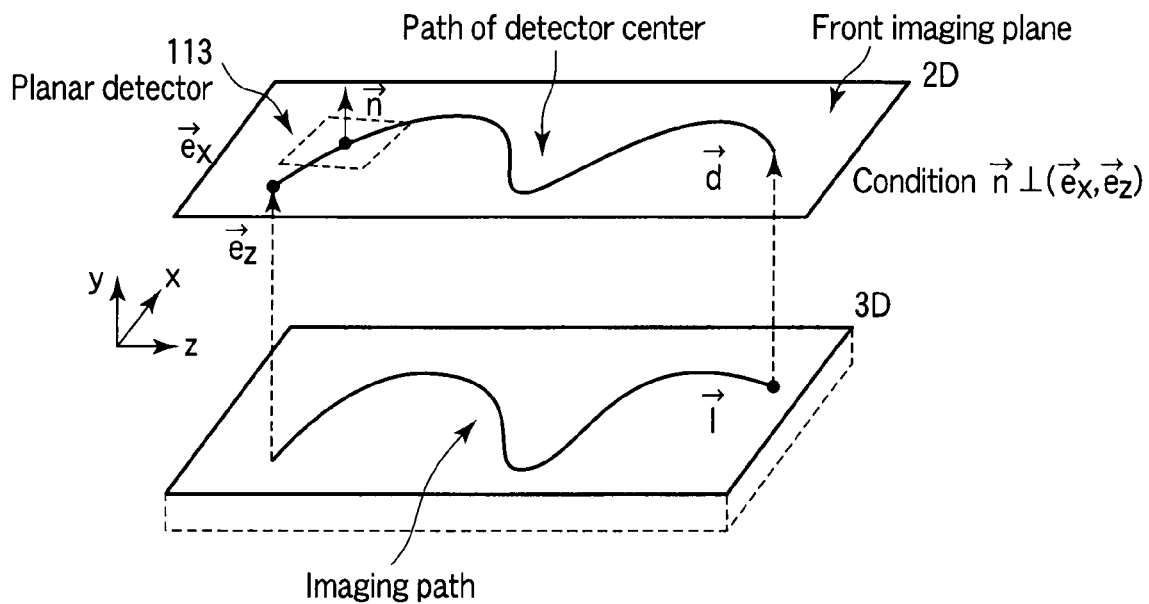
FIG. 3A is a diagram showing the relation between an imaging path l and a movement path d of the center of a planar detector 113, in the first embodiment.
Figure 3B:
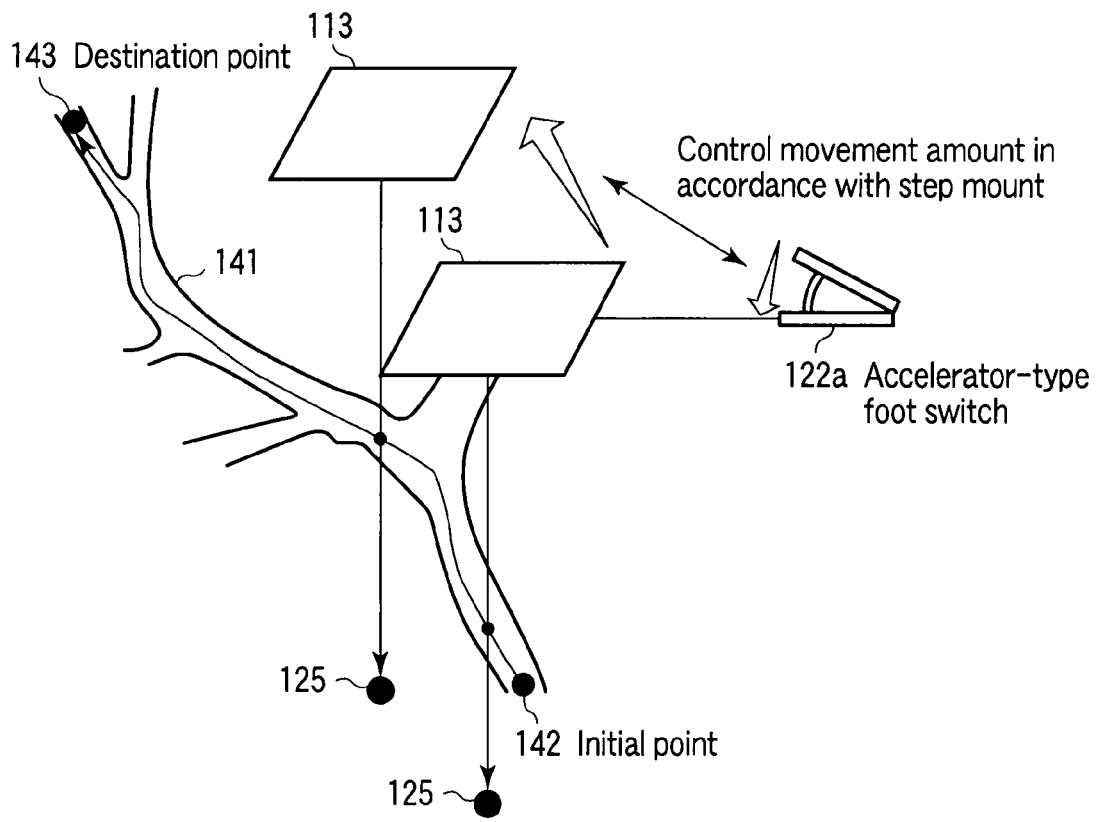
FIG. 3B is a diagram for the explanation of an initial point and a destination point on a vascular map image, in the first embodiment.

FIG. 3A is a diagram showing the relation between an imaging path l and a movement path d of the center of the planar detector 113 in the present embodiment. FIG. 3B is a diagram for the explanation of an initial point and a destination point on a vascular map image.

Furthermore, in step S3, the input device of the operation unit 121 is operated by the user so that three-dimensional coordinates of an initial point 142 and a destination point 143 in a blood vessel 141 are designated on the vascular map image. Then, in step S4, the designated three-dimensional coordinates and map image are transferred to the path calculator 131, and three-dimensional coordinates of a designated path of the holding arm 114 through which a beam center line is to pass are searched for. Here, the beam center line means a line that connects the center of the X-ray generating unit 111 and the center of the planar detector 113. Moreover, the designated path is a set of coordinates which are designated on the map image and through which the beam center passes. The designated path that has been searched for is displayed on the monitor 123. Here, if there are a plurality of designated paths, the user specifies a designated path to be used, among the designated paths that have been searched for by the user using the input device of the operation unit 121.

Then, in step S5, the subject 200 is mounted on the bed 112, and an examination is started.

In step S6, when a coordinate conversion coefficient calculation program is started in accordance with a user instruction, the subject 200 is first imaged. Here, the image that has been taken is recorded in the image data storage circuit 136. Then, the image of the subject and the map image are read into the image calculating circuit 135. The image calculating circuit 135 matches imaging position coordinates represented by Expression (1) to map image coordinates represented by Expression (2), so that a coordinate conversion coefficient in Expression (3) (see Expression (4) and Expression (5)) is calculated.

$$\vec{P} \quad (1)$$

$$\overline{m} \quad (2)$$

$$\vec{P} = \vec{q} + \overline{R} \cdot \vec{m} \quad (3)$$

$$\vec{q} \quad (4)$$

$$\overline{R} \quad (5)$$

Furthermore, in step S7, the coordinate conversion coefficients represented by Expression (4) and Expression (5) are received by the path calculator 131, so that three-dimensional coordinates of the designated path are converted to three-dimensional coordinates of the imaging path. The converted three-dimensional imaging path l is registered in the memory 133 in step S8. Then, in step S9, when the unshown path setting switch in the operation unit 121 is turned off, the setting is completed, and this sequence is finished.

Next, the movement of an imaging position using the imaging position movement amount control switch 122 is described with reference to a flowchart in FIG. 2B.

When this sequence is started, an imaging path following program is first started in the system control unit 110 in accordance with a user instruction in step S11. Then, in step S12, three-dimensional coordinates of the imaging path corresponding to the initial point of the imaging path is read into the mechanism controller 132 from the memory 133, and information on the current position of the holding arm 114 is also read into the mechanism controller 132 from the position sensor 128. Further, a position of the holding arm where the beam center line crosses the imaging path is calculated by the mechanism controller 132, and then a control signal is supplied to the mechanical unit 118. As a result, the holding arm 114 is moved to the initial point 142.

Here, for example, a starting imaging position is set for front imaging, and the front imaging is always maintained in the subsequent operations. That is, in FIG. 3A, vectors (ex, ez) of the plane of the front imaging are always perpendicular to the normal vector n of the planar detector 113. Thus, the movement path d of the detector is two-dimensional.

Then, in step S13, a procedure by the user is started. Here, the user uses an accelerator-type foot switch for speed control as an example of the imaging position movement amount control switch 122. Two kinds of accelerator-type foot switches for forward movement and backward movement are used.

If the user starts stepping on a forward movement or backward movement accelerator-type foot switch 122a, the amount of a step is detected by the system control unit 110, and a signal corresponding to the step amount is supplied to the mechanism controller 132. When the mechanism controller 132 receives the step amount signal, information on the current position of the holding arm 114 is read into the mechanism controller 132 from the position sensor 128, and imaging path coordinates next to the current imaging path coordinates are also read into the mechanism controller 132 from the memory 133. Then, a position of the holding arm where the beam center line crosses the next imaging path coordinates is calculated by the mechanism controller 132.

Figure 4A:
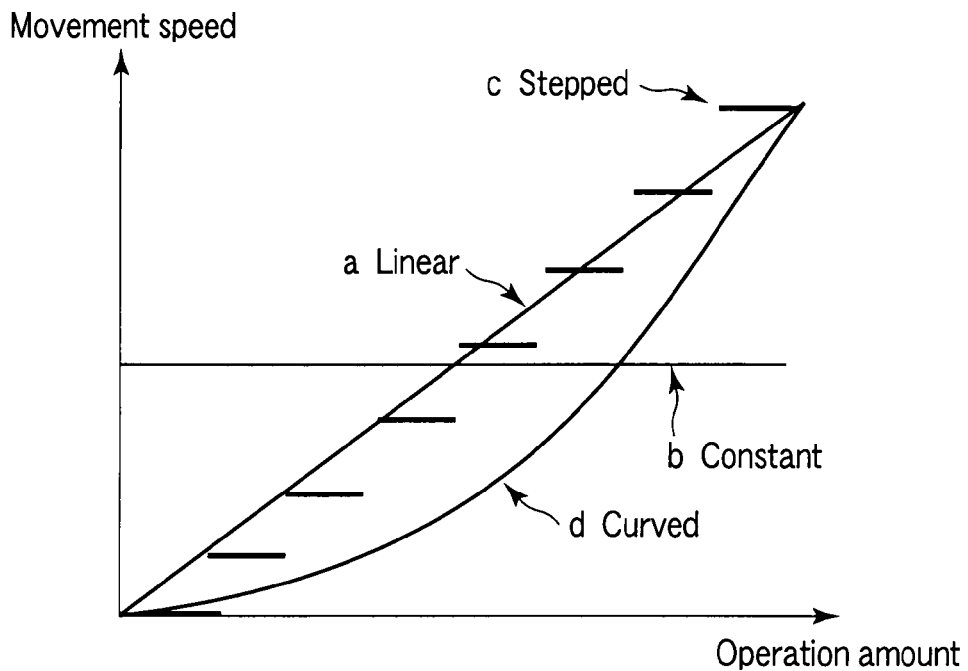
FIG. 4A is a graph showing the relation between the movement speed and operation amount of the movement amount control switch 122.

Furthermore, as shown in FIG. 4A, the mechanical unit 118 calculates a movement speed of the holding arm 114 at which the movement speed of the planar detector 113 has a linear (indicated by a) relation with the step amount signal. Then, a control signal is supplied to the mechanical unit 118, and in step S14, the imaging position is moved from the current position of the holding arm to the next position of the holding arm at the calculated movement speed. If the imaging position has not reached the destination point 143 in step S15, the sequence shifts to step S13, and the processing previously described is repeated. On the contrary, if the imaging position has reached the destination point 143 in step S15, the sequence is finished.

The series of such processing is continued while the accelerator-type foot switch 122a is stepped on. As a result, the imaging position moves on the preset imaging path at a speed corresponding to the step amount. That is, when the user considers that the imaging time at the current imaging position should be short, the step amount is increased so that the imaging position quickly moves to the next imaging position. In contrast, when the user considers that the imaging time should be longer, the step amount is decreased so that the imaging position moves slower.

Furthermore, particularly when imaging should be carried out at the stopped imaging position during the procedure performed by the user, the user releases the accelerator-type foot switch 122a. Then, the supply of the step amount signal from the system control unit 110 to the mechanism controller 132 is stopped, and the imaging position is stopped on the spot.

In addition, imaging may be operated with any timing independently of the change of the imaging position using the accelerator-type foot switch 122a.

Thus, the simple operation of the accelerator-type foot switch 122a during the procedure makes it possible to successively change the imaging position while always capturing, in an imaging field, a preset path where imaging should be performed. Moreover, the movement speed of the imaging position can be changed to freely adjust the imaging time at each imaging position.

Although an imaging path is determined from the map image in the explanation described above, an imaging path such as an imaging path used in the past may only be read from the outside and used.

Figure 5A:
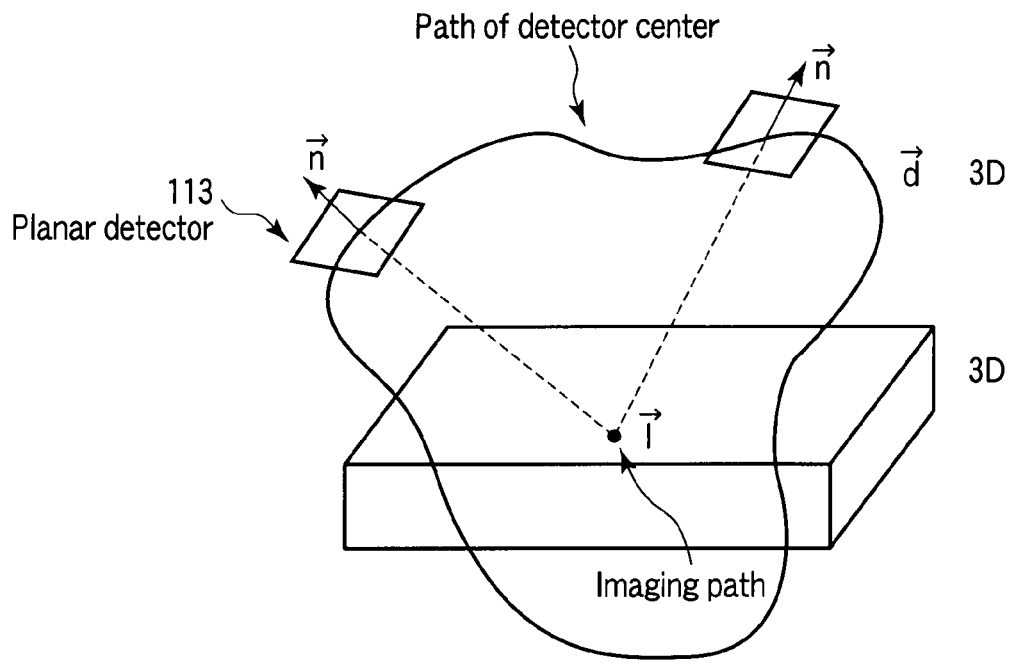
FIG. 5A is a diagram showing the relation between the imaging path l and the movement path d of the center of the planar detector 113 in the case where an imaging path is a point in the first embodiment.
Figure 5B:
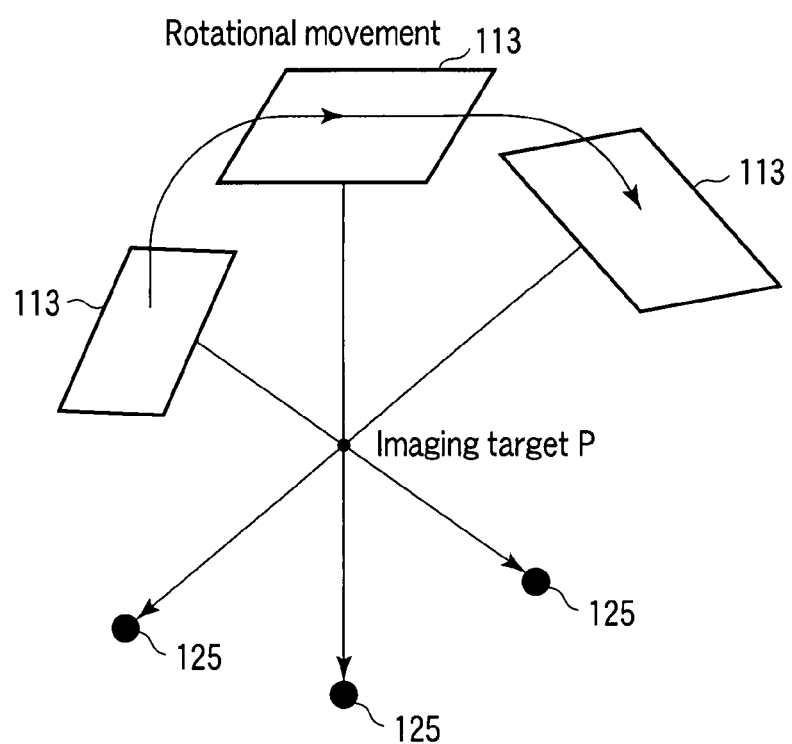
FIG. 5B is a diagram showing the change of the imaging position in the case where an imaging path is a point in the first embodiment.

Furthermore, a three-dimensional curve is taken as an example to explain the imaging path above. However, the imaging path may be a point as shown in FIG. 5A. In this case, instead of registering the three-dimensional coordinates of the imaging path in the memory 133, a series of imaging angles serving as desired projection directions is registered in the memory 133. Thus, the imaging position in this case changes in such a manner as to three-dimensionally rotate around the imaging path (imaging target) as shown in FIG. 5A.

In addition, there are two kinds of accelerator-type foot switches 122a for forward movement and backward movement in the above explanation. However, there may be one accelerator-type foot switch 122a that switches between forward movement and backward movement in the following manner. That is, the above-described operation is performed to make a forward movement. In order to make a backward movement, the user steps on the foot switch 122a quickly to the end, so that a step amount per unit time is detected by the system control unit 110. If the step amount is beyond a set threshold, a backward movement signal and a step amount signal are supplied to the mechanism controller 132. When the mechanism controller 132 receives the backward movement signal and the step amount signal, an imaging position in imaging path coordinates preceding the imaging path coordinates of the current position is calculated in the same manner as described above.

Figure 4B:
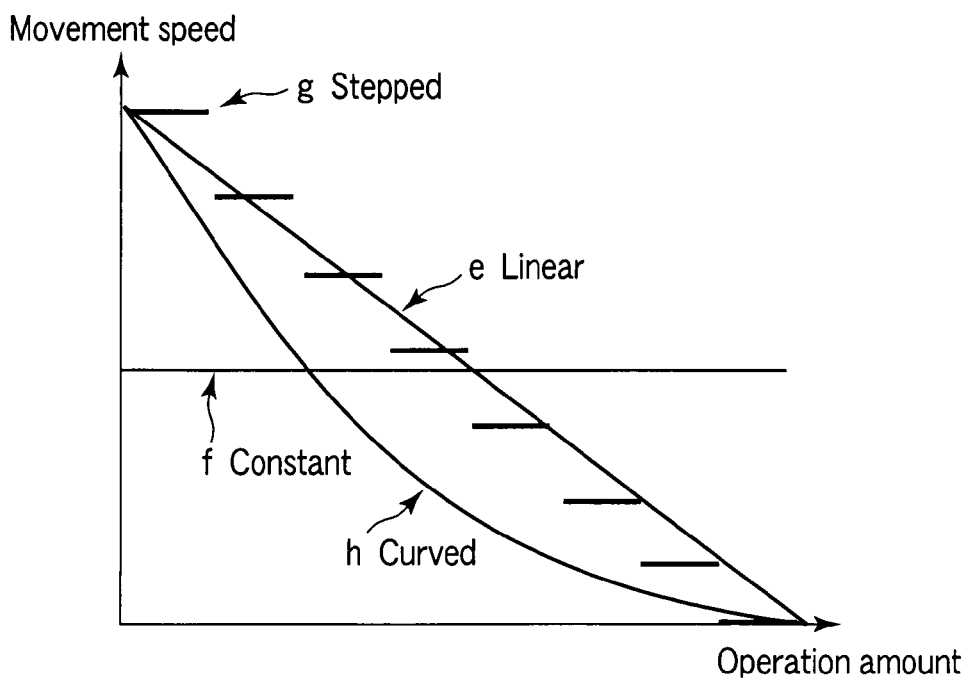
FIG. 4B is a graph showing the relation between the movement speed and operation amount of the movement amount control switch 122.

Furthermore, when the backward movement signal is received, the relation of the movement speed of the planar detector 113 with the step amount signal may be inverted with respect to the relation in the case of forward movement to calculate a movement speed of the holding arm as shown in FIG. 4B. Alternatively, the relation of the movement speed of the planar detector 113 with the step amount signal that varies between the forward movement and the backward movement may be used.

Still further, the relation of the movement speed of the planar detector 113 with the step amount signal is linear (indicated by a and e) in the above explanation. However, as shown in FIG. 4A and FIG. 4B, the relation therebetween may be constant (indicated by b and f), stepped (indicated by c and g) or curved (indicated by d and h). Moreover, the movement speed may be changed in accordance with an operation amount such as the number of times of steps instead of the step amount.

Further yet, the amount of a step on the foot switch 122a is matched to the movement speed of the planar detector 113 to calculate a movement speed of the holding arm in the above explanation. However, the amount of a step on the foot switch 122a may be matched to the acceleration of the planar detector 113 to calculate a movement speed of the holding arm.

In addition, the movement amount control switch is the accelerator-type foot switch 122a in the above explanation, but may be the following switch. For example, the movement amount control switch may be a trigger-type switch in the shape of a remote controller that can be held by hand, a lever-shaped switch, a rotary switch such as a jog dial, or a planar switch that uses compression or capacitance. The movement amount control switch is not exclusively a physical switch, and may be a software-enabled switch such as a control bar displayed on a screen.

(Second Embodiment)

Next, a second embodiment of the present invention is described.

In the second embodiment, an example of orthogonal rotation of an imaging position with respect to an imaging path is described.

While the imaging position is translated in such a manner as to always maintain the position of the front imaging in the first embodiment described above, there may be a case where an observation should be made in a direction perpendicular to the imaging path and from a given angle. In the second embodiment, in order to meet this demand, means of controlling the operation of rotating the imaging position in a direction perpendicular to the imaging path is added to the system in the first embodiment described above.

In addition, the basic configuration and operation of an X-ray diagnostic apparatus in the embodiment described from now on are the same as the basic configuration and operation of the X-ray diagnostic apparatus in the first embodiment described above. Therefore, to avoid redundant explanations, like parts are provided with like reference numbers and are neither shown nor described later, and different parts and operations are only described.

FIG. 6 is a flowchart for the explanation of processing performed under the control of a system control unit 110 in the X-ray diagnostic apparatus according to the second embodiment of the present invention. FIG. 7A is a diagram showing the relation between an imaging path l and a movement path d of the center of a planar detector 113, according to the second embodiment. FIG. 7B is a diagram for the explanation of an initial point and a destination point on a vascular map image, in the second embodiment.

When this sequence is started, an orthogonal rotation switch (not shown) in an operation unit 121 is first turned on by a user in step S121, so that an imaging angle changing program is started. Then, in step S22, simultaneously with the start of this program, information on the current position of a holding arm 114 and information on the vertical position of a bed 112 that are derived from a position sensor 128 are stored in a memory 133 as an original imaging position Pb.

Then, in step S23, the information on the current position of the holding arm, the information on the vertical position of the bed, and the imaging path are input to a mechanism controller 132 from the memory 133. On the basis of such data, the mechanism controller 132 calculates an imaging position where a beam center line (the normal vector n of the planar detector 113) intersects at right angles with a tangent l' to the imaging path, and also calculates a vertical position of the bed where the intersection point of the beam center line and the imaging path is isocentric. At this point, the imaging position where the beam center line intersects at right angles with the imaging path is calculated in a plane created by the tangent at the intersection point of the beam center line and the imaging path, as shown in FIG. 7B.

When the imaging position and the vertical position of the bed are thus calculated in the mechanism controller 132, a control signal is supplied to a mechanical unit 118, so that the position of the holding arm and the position of the bed are changed in step S24.

Then, in step S25, when an imaging angle changing switch (not shown) in the operation unit 121 is operated by the user, an operation signal is input to the mechanism controller 132 through the system control unit 110, and an imaging angle $\theta$ to be changed is calculated accordingly. Further, the mechanism controller 132 calculates an imaging position whereby the condition in which the tangent l' to the imaging path intersects at right angles with the normal vector n of the detector is satisfied and whereby the imaging angle is changed $\theta$. Then, in step S26, a control signal is supplied to the mechanical unit 118, so that the position of the holding arm 114 is changed, and the imaging position is changed at an angle $\theta$ in a direction perpendicular to the imaging path.

Consequently, the simple operation of the switch makes it possible to obtain an imaging position perpendicular to the imaging path. Moreover, the imaging angle can be freely changed in such a manner as to maintain the perpendicular imaging position.

Then, when imaging is performed in step S27, whether the imaging has ended is judged in step S28. If the imaging is still continued here, the unshown orthogonal rotation switch is operated again, and the sequence shifts to step S25, and then the processing previously described is repeated. On the contrary, if the imaging at the changed imaging angle is finished, the unshown orthogonal rotation switch is turned off. Then, in step S29, the original imaging position Pb is read into the mechanism controller 132 from the memory 133, and a control signal is supplied to the mechanical unit 118, so that the imaging position returns to the same imaging position Pb as the position before the start of the imaging angle changing program. Thus, the sequence is finished.

As described above, the user can automatically determine an imaging position perpendicular to the imaging path by one simple switch operation, so that the time of a procedure can be reduced.

Moreover, the orthogonal rotation switch is used in the above explanation. However, the switch is not exclusively a physical switch, and may be a button on a display screen or a switch enabled by speech recognition.

(Third Embodiment)

Next, a third embodiment of the present invention is described.

In the first embodiment described above, an initial point and an end point (destination point) are designated, and a movement is made along the determined imaging path in such a manner as to perform imaging at the same time. However, there may be a case where the user is interested in a branch portion of the imaging path. In the third embodiment, in order to meet this demand, the following are added to the system in the first embodiment: a branch portion identifier 129 for identifying a branch portion of the imaging path; a function for storing imaging positions at the branch portions from an initial point to a destination point in order; and a switch for reproducing a stored imaging position.

FIGS. 8A and 8B are flowcharts for the explanation of processing performed under the control of a system control unit 110 in an X-ray diagnostic apparatus according to the third embodiment. FIG. 9A is a diagram showing the relation between an imaging path l and a movement path d of the center of a planar detector 113, in the third embodiment. FIG. 9B is a diagram for the explanation of an initial point and a destination point on a vascular map image, in the third embodiment.

In the third embodiment, the imaging position skips to the branch portion in such a manner as to maintain front imaging, so that the movement path d of the planar detector 113 has a two-dimensional discrete value.

The operation of registering imaging position coordinates of the branch portion is described below.

In addition, processing in steps S31 to S34, S36 to S37 and S40 in the flowchart of FIG. 8A is the same as the processing in steps S1 to S4, S5 to S6 and S9 in the flowchart of FIG. 2A in the first embodiment, and is not therefore described here. Instead, the processing of the corresponding step numbers is referred to.

After a designated path has been specified by a path calculator 131 in steps S34, three-dimensional coordinates of the branch portion are extracted by the branch portion identifier 129 on the basis of three-dimensional coordinates of the designated path derived from the path calculator 131 and on the basis of a map image in step S35. Then, in step S36, the three-dimensional coordinates of the branch portion are input to the path calculator 131. Then, in step S37 and step S38, the path calculator 131 converts the coordinates to branch portion imaging position coordinates which are in a system-owned coordinate system, as in the first embodiment described above. The branch portion imaging position coordinates are registered in a memory 133 in step S39 together with the order of the branch portion from the initial point. Then, when setting is completed in step S40, the sequence is finished.

Next, the change of the imaging position using a branch portion imaging switch is described with reference to the flowchart in FIG. 8B.

In addition, the front imaging is always maintained in the subsequent operations.

Described is the case where the unshown branch portion imaging switch in the operation unit 121 is operated in the middle of the operation in the first embodiment described above.

After entrance into this sequence, the unshown branch portion imaging switch in the operation unit 121 is operated in step S41. Then, in step S42, a mechanism controller 132 calculates closest branch portion imaging position coordinates toward the end point (destination point) in accordance with the branch portion imaging position coordinates derived from the memory 133 and the current imaging position coordinates derived from the position sensor 128. Further, the mechanism controller 132 calculates an imaging position where a beam center line intersects with the branch portion imaging position coordinates.

Then, in step S43, a control signal is supplied to a mechanical unit 118, so that the imaging position skips to the branch portion.

As described above, the user can, by one simple switch operation, preemptively bring the imaging position to the branch portion to be imaged, so that the time of a procedure can be reduced.

Moreover, the branch portion imaging switch is used in the above explanation. However, the switch is not exclusively a physical switch, and may be a button on a display screen or a switch enabled by speech recognition.

(Fourth Embodiment)

The operation of imaging a branch portion from an optimum imaging angle is described in a fourth embodiment.

There may be a case where a branch portion should be imaged from an angle at which the branch portion is most easily viewed. In the third embodiment described above, the imaging position can be moved to the branch portion, but the imaging angle remains set for the front imaging. In order to solve this problem, in the fourth embodiment, the following are added to the system in the third embodiment: a function for storing an imaging angle identifier 130 which identifies an optimum branch portion imaging angle and also storing its optimum imaging angle; and a switch for reproducing a stored optimum imaging angle.

Figure 11A:
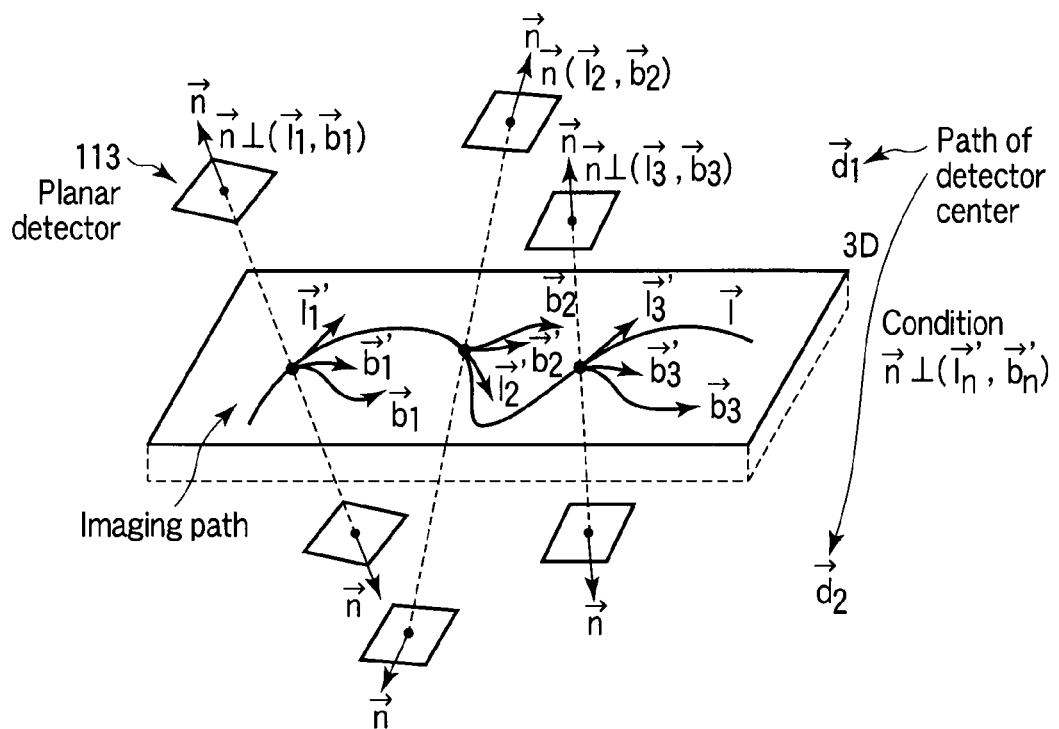
FIG. 11A is a diagram showing the relation between an imaging path l and a movement path d of the center of a planar detector 113, in the fourth embodiment.
Figure 11B:
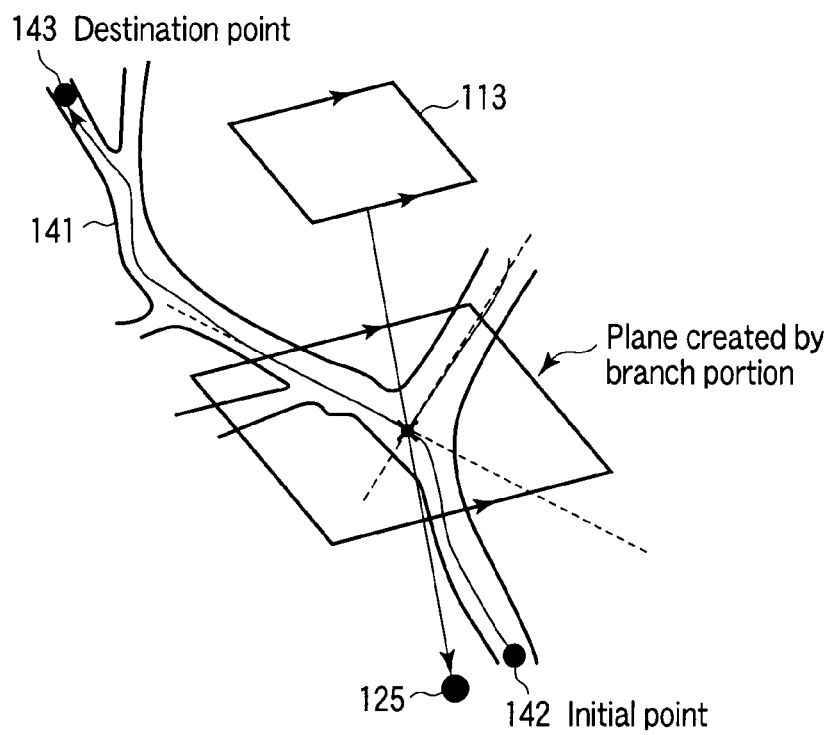
FIG. 11B is a diagram for the explanation of an initial point and a destination point on a vascular map image, in the fourth embodiment.

FIGS. 10A and 10B are flowcharts for the explanation of processing performed under the control of a system control unit 110 in an X-ray diagnostic apparatus according to the fourth embodiment. FIG. 11A is a diagram showing the relation between an imaging path l and a movement path d of the center of a planar detector 113, in the fourth embodiment. FIG. 11B is a diagram for the explanation of an initial point and a destination point on a vascular map image, in the fourth embodiment.

In addition, processing in steps S51 to S55, S57 to S59 and S61 in the flowchart of FIG. 10A is the same as the processing in steps S31 to S35, S36 to S38 and S40 in the flowchart of FIG. 8A in the third embodiment, and is not therefore described here. Instead, the processing of the corresponding step numbers is referred to.

In the fourth embodiment, as in the third embodiment described above, the imaging angle identifier 130 calculates an optimum imaging angle of the branch portion in accordance with information on three-dimensional coordinates of a designated path, a map image and three-dimensional coordinates of the branch portion derived from a branch portion identifier 129 in step S56, after the extraction of the three-dimensional coordinates of the branch portion has been finished in steps S51 to S55.

Here, the optimum imaging angle is an angle at which the normal vector n of the planar detector 113 intersects at right angles with a branch plane created by a tangent ln' in a branch portion ln and a tangent bn' to a branch path direction bn. Here, two angles reverse 180 degrees to each other are obtained. Then, after steps S57 to S59, this optimum imaging angle is registered in a memory 133 in association with the branch portion imaging position coordinates in step S60. Then, when setting is completed in step S61, the sequence is finished.

Next, imaging using a branch portion optimum imaging angle switch is described with reference to the flowchart in FIG. 10B.

Described is the case where the branch portion optimum imaging angle switch (not shown) in an operation unit 121 is operated in the middle of the operation in the first embodiment described above.

After entrance into this sequence, the unshown branch portion optimum imaging angle switch in the operation unit 121 is operated in step S71. Then, in step S72, a mechanism controller 132 calculates a closest branch portion imaging position from the current imaging position toward the end point (destination point), as in the third embodiment described above. Then, in step S73, an optimum imaging angle having the smallest amount of the change of the imaging angle from the current imaging angle is determined in accordance with the optimum imaging angles of the two imaging branch portions read from the memory 133 and in accordance with information on the current imaging angle derived from a position sensor 128.

When the closest branch portion imaging position and the optimum imaging angle are determined, a control signal is supplied to a mechanical unit 118, so that a holding arm 114 is moved, and the imaging position and the angle are changed, in step S74.

As a result, the user can, by one simple switch operation, preemptively bring the imaging position to the branch portion to be imaged. At the same time, an imaging angle at which the branch portion is most easily observed can be set. Thus, the time of a procedure can be reduced.

Moreover, the branch portion optimum imaging angle switch is used in the above explanation. However, the switch is not exclusively a physical switch, and may be a button on a display screen or a switch enabled by speech recognition.

(Fifth Embodiment)

Next, a fifth embodiment of the present invention is described.

While the holding arm 114 is translated in such a manner as to always maintain the front imaging position in the first embodiment described above, there may be a case where an imaging position should be changed while imaging is being performed from a direction perpendicular to the imaging path. In order to meet this demand, in the fifth embodiment, an orthogonal movement imaging switch is added to the system in the first embodiment described above.

Figure 12A:
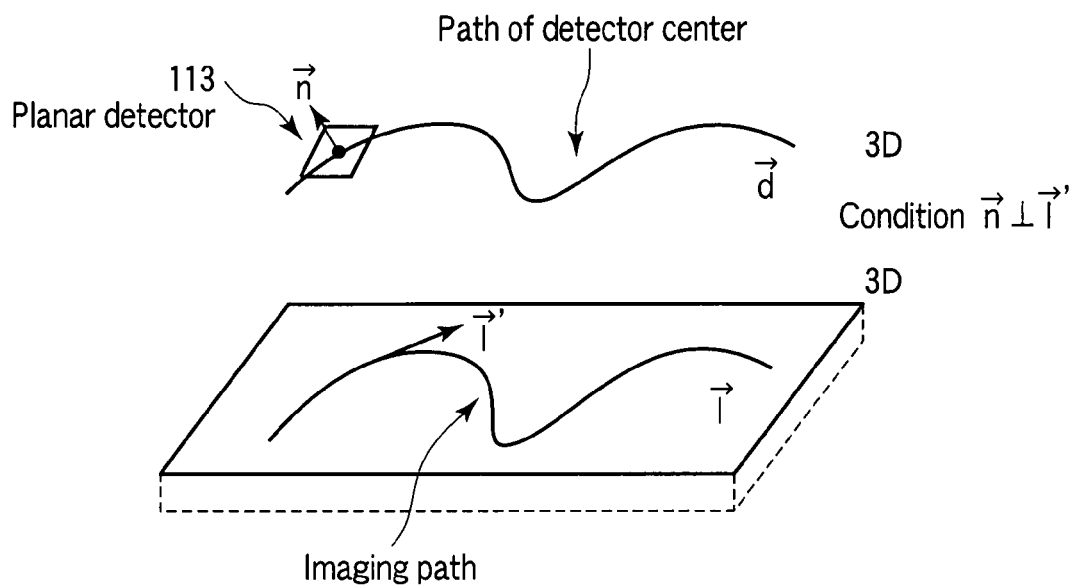
FIG. 12A is a diagram showing the relation between an imaging path l and a movement path d of the center of a planar detector 113, in the fifth embodiment.
Figure 12B:
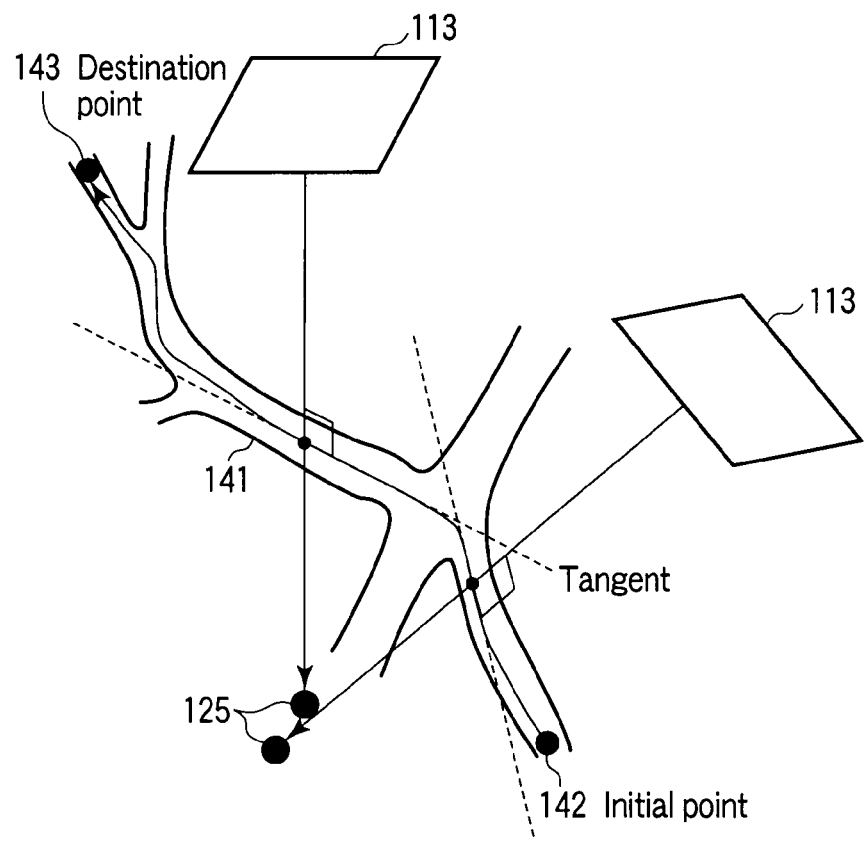
FIG. 12B is a diagram for the explanation of an initial point and a destination point on a vascular map image, in the fifth embodiment.

FIG. 12A is a diagram showing the relation between an imaging path l and a movement path d of the center of a planar detector 113, in the fifth embodiment. FIG. 12B is a diagram for the explanation of an initial point and a destination point on a vascular map image, in the fifth embodiment.

When the unshown orthogonal movement imaging switch in an operation unit 121 is operated by a user, an orthogonal movement imaging program is started. Then, information on the position of a holding arm at the current imaging position derived from a position sensor 128 and three-dimensional coordinates of the imaging path derived from a memory 133 are input to a mechanism controller 132. On the basis of such data, the mechanism controller 132 calculates an imaging position where a beam center line (the normal vector n of the planar detector 113) intersects at right angles with a tangent l' to the imaging path. At this point, the imaging position where the beam center line intersects at right angles with the imaging path is calculated in a plane created by the tangent at the intersection point of the beam center line and the imaging path.

When the imaging position is calculated in the mechanism controller 132, a control signal is supplied to a mechanical unit 118, so that the position of the holding arm 114 is changed. Then, as in the first embodiment described above, the user operates a movement amount control switch 122 to change the imaging position. Thus, imaging path coordinates next to the current imaging path coordinates are also read into the mechanism controller 132 from the memory 133, in addition to the calculation of the movement amount in the first embodiment. Then, the mechanism controller 132 calculates an imaging position where a beam center line (the normal vector n of the planar detector 113) in the next imaging path coordinates intersects at right angles with a tangent l' to the imaging path. Subsequently, a control signal is supplied to the mechanical unit 118.

As described above, the movement amount control switch 122 is used to change the imaging position, and at the same time, imaging can be always performed from an angle perpendicular to the imaging path by simply pressing the switch.

Moreover, the orthogonal movement imaging switch is used in the above explanation. However, the switch is not exclusively a physical switch, and may be a button on a display screen or a switch enabled by speech recognition.

(Sixth Embodiment)

Next, a sixth embodiment of the present invention is described.

While the initial point and the destination point of the imaging position are designated to calculate an imaging position on an imaging path in the first to fifth embodiments described above, an imaging (projection) direction is determined in accordance with a preset order in the sixth embodiment.

In general, blood vessels that perfuse a heart muscle are located outside the heart muscle. Therefore, perpendicularly applying X rays to the heart muscle is substantially equal to causing a line connecting the blood vessels on the surface of the heart muscle to the center of the heart to nearly coincide with the projector of the X rays.

Figure 13:
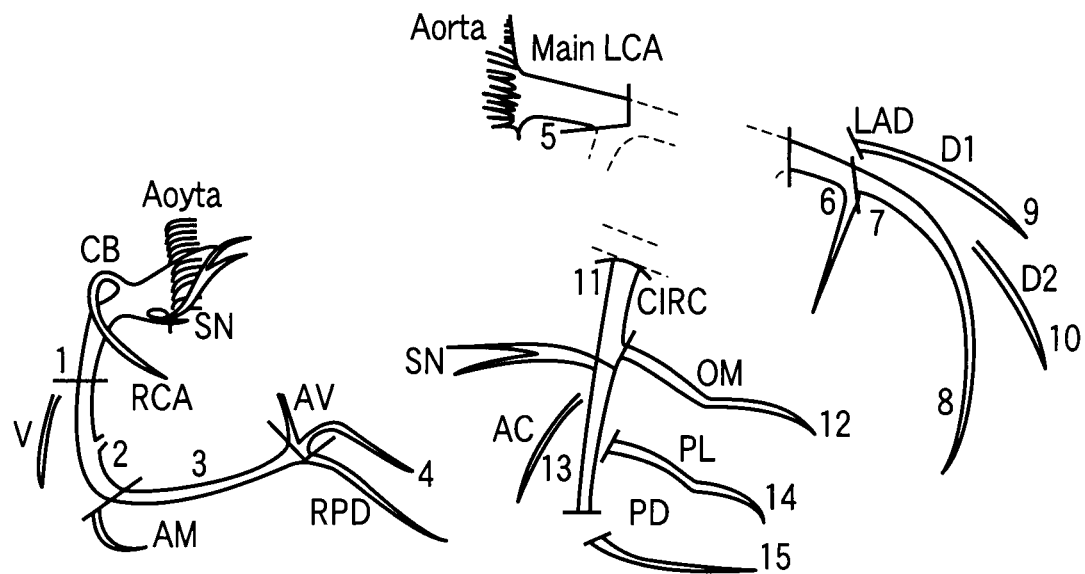
FIG. 13 is a diagram for the explanation of an example of AHA-based blood vessel classification numbers.
Figure 14:
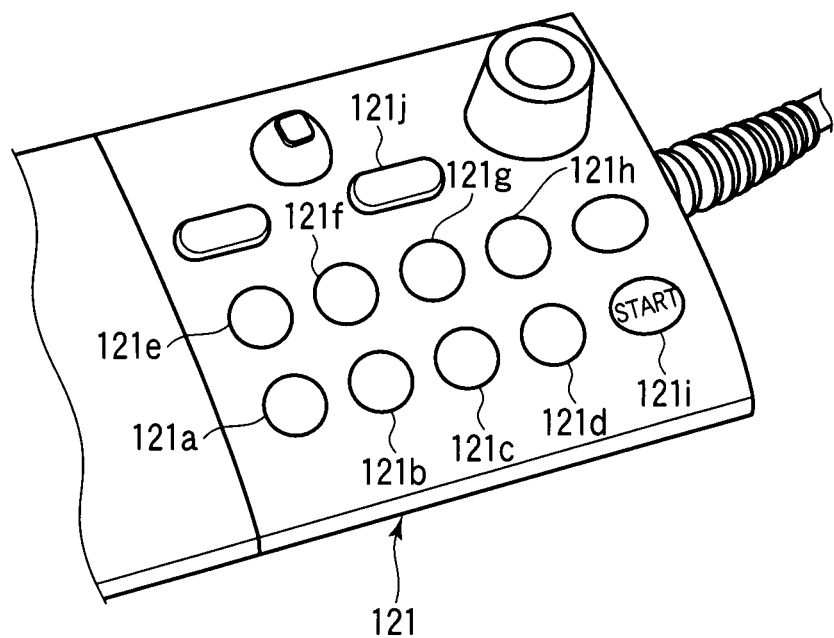
FIG. 14 is a diagram showing an example of operation buttons provided in an operation unit 121 of an X-ray diagnostic apparatus according to a sixth embodiment of the present invention.

Here, anatomically allocated blood vessel numbers recommended by American Heart Association (AHA) are used. As shown in FIG. 13, in accordance with AHA classification, numbers 1 to 15, for example, are assigned to blood vessels in the case of heart vessels. These AHA vessel classification numbers are previously registered in a memory 133 in an imaging path calculating unit 116. Moreover, as shown in FIG. 14, an operation unit 121 is provided with, for example, operation buttons 121a to 121j corresponding to the AHA vessel classification numbers.

Figures 15A, 15B:
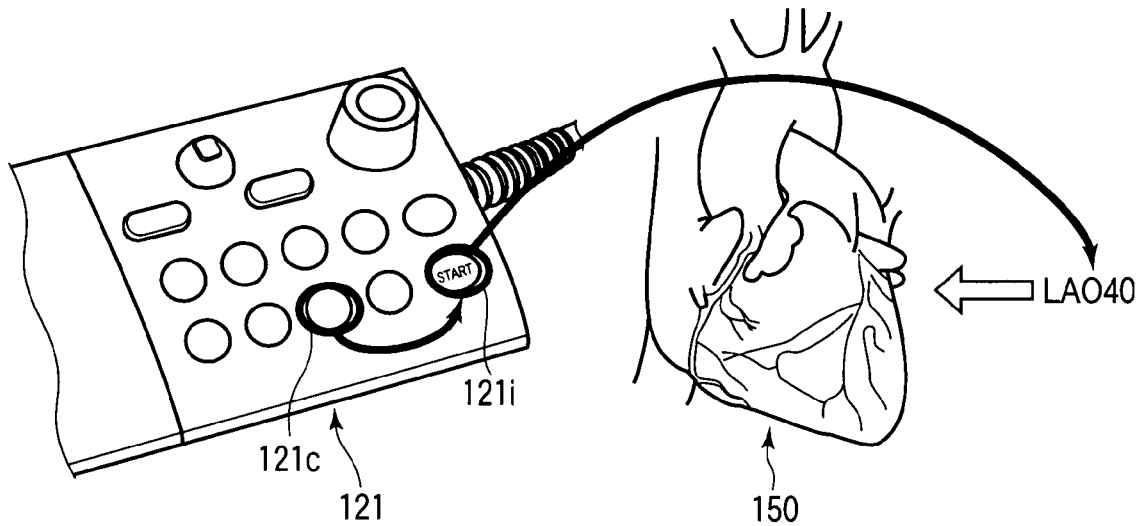
FIG. 15A is a diagram showing an example of the operation of the operation buttons in the sixth embodiment.
FIG. 15B is a diagram showing an imaging direction in the case where the operation buttons in FIG. 15A are operated.

For example, as shown in FIG. 15A, if the operation button 121c is pressed, the projection direction of an X-ray generating unit 111 is set to be perpendicular to a vessel portion of the AHA vessel classification number "2". That is, information on the position of a holding arm at the current imaging position derived from a position sensor 128 and information on the AHA vessel classification number derived from a memory 133 are input to a mechanism controller 132. On the basis of such data, the mechanism controller 132 calculates a position perpendicular to the vessel portion of the AHA vessel classification number ("2" in this case). When the imaging position is calculated in the mechanism controller 132, a control signal is supplied to a mechanical unit 118, so that the position of the holding arm 114 is changed. Then, as shown in FIG. 15B, imaging is enabled at the position perpendicular to the vessel portion of the AHA vessel classification number "2".

In addition, when there are two directions perpendicular to the vessel portion, these directions are preferably input by the user in advance. Alternatively, a direction may be selectable at the time.

Moreover, an imaging direction is not exclusively perpendicular. For example, when a portion located in the vicinity of a blood vessel of the AHA vessel classification number "3" should be observed, the user may preset a desired angle.

As described above, imaging can always be performed from a direction perpendicular to a desired vessel portion by simply operating the button corresponding to the anatomically allocated blood vessel number.

(Seventh Embodiment)

In the sixth embodiment described above, the imaging direction is determined exclusively by the heart muscle to be viewed by the user or by the portion of the blood vessel number. However, the present invention is not exclusively limited to the portion of the blood vessel number. In a seventh embodiment, imaging can be performed at a part between a plurality of blood vessel numbers.

For example, there may be a case where the heart muscle located around a part between the AHA vessel classification numbers "2" and "3" should be viewed out of a region dominated by right coronary arteries. In this case, according to a conventional method, an imaging system cannot be moved to a desired position and therefore has to be manually moved.

Thus, in the seventh embodiment, the numbers of operation buttons of an operation unit 121 correspond to the AHA vessel classification numbers as in the sixth embodiment described above. Moreover, a plurality of desired operation buttons are pressed in order so that imaging directions are set between a plurality of AHA vessel classification numbers.

Figures 16A, 16B:
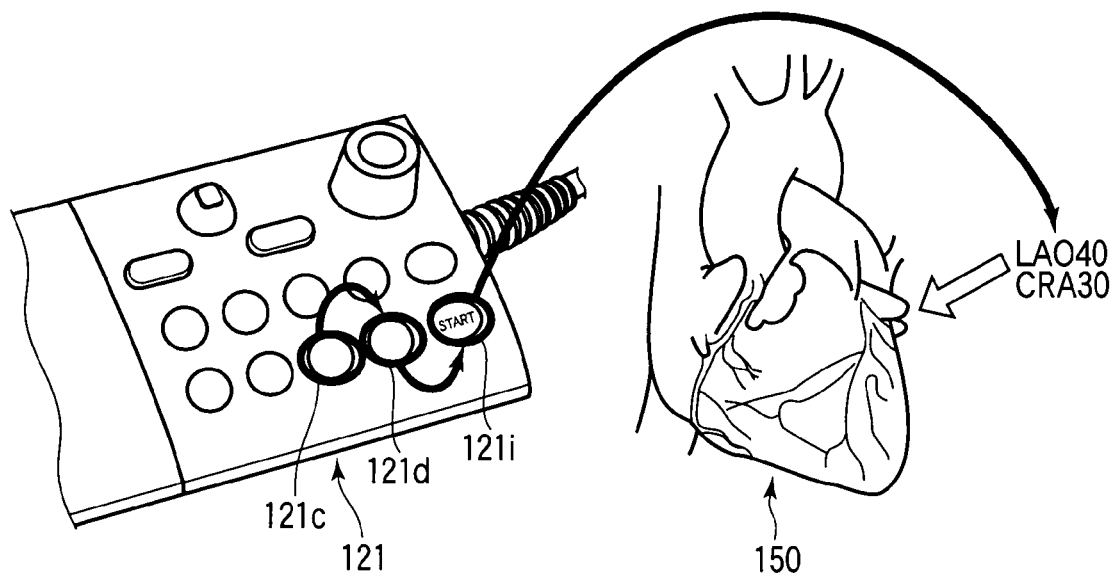
FIG. 16A is a diagram showing an example of the operation of operation buttons in a seventh embodiment of the present invention.
FIG. 16B is a diagram showing an imaging direction in the case where the operation buttons in FIG. 16A are operated.

For example, as shown in FIG. 16A, a start button 121i is pressed after operation buttons 121c and 121d of the operation unit 121 are pressed. Then, as shown in FIG. 16B, an X-ray imaging position is set to be perpendicular to a part between the AHA vessel classification numbers "2" and "3".

Consequently, if a plurality of buttons are pressed among the buttons corresponding to the anatomically allocated blood vessel numbers, an X-ray imaging direction can be set in the center-of-gravity direction of the imaging direction for each tissue.

(Eighth Embodiment)

In the sixth and seventh embodiments, the portions to be viewed by the user are limited to the parts corresponding to the AHA vessel classification numbers or parts between these numbers. However, in actual clinical scenes, the heart muscle to be viewed is not limited to a part of a certain blood vessel number. For example, when a certain blood vessel has stenosis, all heart muscles far from the stenosis should be observed in many cases. In such cases, a single direction is not enough. An eighth embodiment makes it possible to observe all the target heart muscles in a licking manner.

According to a conventional method, an imaging system can be manually rotated, but deviates from a visual field or is not perpendicular when operated by an inexperienced person. Thus, in the eighth embodiment, the numbers of operation buttons of an operation unit 121 correspond to the AHA vessel classification numbers so that an angle at which an observation is easily made is set in the order of the pressing of the operation buttons.

Figures 17A, 17B:
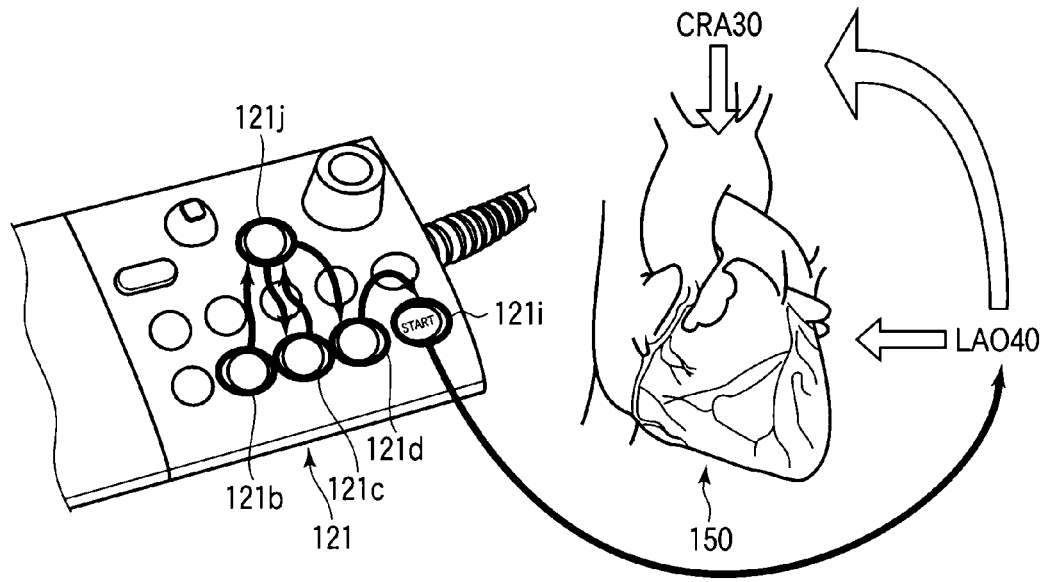
FIG. 17A is a diagram showing an example of the operation of operation buttons in an eighth embodiment of the present invention.
FIG. 17B is a diagram showing an imaging direction in the case where the operation buttons in FIG. 17A are operated.

For example, as shown in FIG. 17A, suppose that the operation buttons of the operation unit 121 are pressed in the following order: an operation button 121b→a map button 121j→an operation button 121c→the map button 121j→an operation button 121d→a start button 121i. Then, as shown in FIG. 17B, the following route is set: an angle at which a part located in the vicinity of the AHA vessel classification number "1" is easily viewed is first set, and the route then shifts to an angle at which a part located in the vicinity of the AHA vessel classification number "2" is easily viewed, and further shifts to an angle at which a part located in the vicinity of the AHA vessel classification number "3" is easily viewed. For example, the AHA blood vessel numbers "1"→"2"→"3" specifically indicate right coronary arteries. For example, a holding arm 114 is rotated in such a manner as "LAO40, CRA0→LAO0, CRA30".

Figures 18A, 18B:
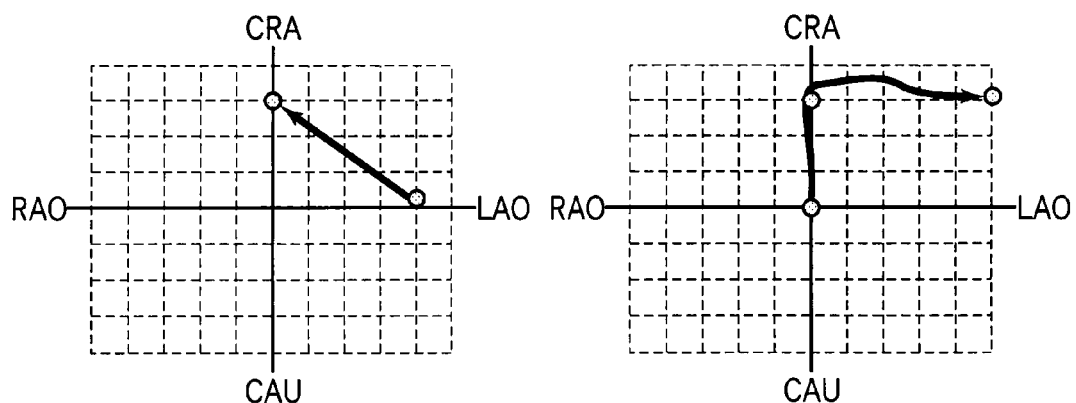
FIG. 18A is a diagram showing an example of the movement of an imaging direction in a right coronary artery in the eighth embodiment.
FIG. 18B is a diagram showing an example of the movement of an imaging direction in a left coronary artery in the eighth embodiment.

FIG. 18A is a diagram showing an example of the movement of an imaging direction in a right coronary artery in the eighth embodiment. FIG. 18B is a diagram showing an example of the movement of an imaging direction in a left coronary artery in the eighth embodiment.

Thus, by successively pressing a plurality of buttons corresponding to the anatomically allocated blood vessel numbers, the route of the imaging directions can be set so that an optimum imaging direction may be obtained for each tissue.

As described above, according to an X-ray diagnostic apparatus in the eighth embodiment, the user can successively change the imaging position along desired imaging positions by simply operating a movement amount control switch or the operation unit. Moreover, only by using the switch, the imaging position can be preemptively brought to the branch portion, and an optimum imaging angle can be set. Thus, troublesome top plate operation and arm angle manipulation which have heretofore been individually required can be simplified.

As a result, for example, not only a reduced inter-procedure condition but also a reduced burden on doctors and an accurate procedure can be advantageously expected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
    imaging means including an X-ray application unit which applies X-rays to a subject and an X-ray detection unit which detects the X-rays applied from the X-ray application unit to pick up a medical image;
    path calculating means for obtaining a path of an imaging position for the subject on the basis of a map image;

a storage unit which stores the path;

imaging system moving means for movably supporting the imaging means to capture the imaging position in an imaging field; and movement control means for moving the imaging system moving means to successively move the imaging position along the path.

2. The X-ray diagnostic apparatus according to claim 1, further comprising:

a bed provided with a top plate on which the subject is mounted, wherein the imaging system moving means includes a rotational operation control unit which controls a rotational operation perpendicular to the axial direction of the path, and a moving mechanism which moves the top plate to always capture, in the imaging field, a path predetermined for the rotational operation.

3. The X-ray diagnostic apparatus according to claim 1, wherein the imaging system moving means includes a substantially C-shaped arm which supports the X-ray application unit and the X-ray detection unit, a support mechanism which rotatably supports the substantially C-shaped arm, and a rotational driving unit which drives the rotation of the substantially C-shaped arm; and the movement control means obtains rotation angles of the substantially C-shaped arm at a plurality of positions on the path on the basis of an image within the map image, and controls the rotation angle of the substantially C-shaped arm at each position accordingly.

4. The X-ray diagnostic apparatus according to claim 1, further comprising:

branch portion designating means for designating a branch portion in the map image and then storing coordinates of the branch portion in the storage unit, wherein the movement control means moves the imaging system moving means in accordance with the coordinates stored in the storage unit.

5. The X-ray diagnostic apparatus according to claim 1, further comprising:

imaging angle designating means for designating an imaging angle parallel to a branch plane at a branch portion in the map image, wherein the movement control means moves the imaging system moving means in accordance with the imaging angle designated by the imaging angle designating means.

6. The X-ray diagnostic apparatus according to claim 1, wherein the movement control means includes an accelerator-type foot switch which is configured to control, in accordance with a step amount thereof, the movement amount of the imaging system moving means.

7. An X-ray diagnostic apparatus comprising:

imaging means including an X-ray application unit which applies X-rays to a subject and an X-ray detection unit which detects the X-rays applied from the X-ray application unit to pick up a medical image;

extracting means for extracting a blood vessel of the subject from a map image;

imaging system moving means for movably supporting the imaging means;

movement control means for moving the imaging system moving means to successively move the imaging position for the subject along the extracted blood vessel; and imaging control means for picking up a moving image by the imaging means during the movement of the imaging system moving means.

8. The X-ray diagnostic apparatus according to claim 7, wherein the imaging system moving means includes a substantially C-shaped arm which supports the X-ray application unit and the X-ray detection unit, a support mechanism which rotatably supports the substantially C-shaped arm, and a rotational driving unit which drives the rotation of the substantially C-shaped arm; and the movement control means extracts a branch portion of a blood vessel in the map image, and rotationally moves the substantially C-shaped arm so that an X-ray projector is set substantially perpendicularly to the branch portion.

9. The X-ray diagnostic apparatus according to claim 7, wherein the imaging system moving means includes a substantially C-shaped arm which supports the X-ray application unit and the X-ray detection unit, a support mechanism which rotatably supports the substantially C-shaped arm, and a rotational driving unit which drives the rotation of the substantially C-shaped arm; and the movement control means rotationally moves the substantially C-shaped arm so that an X-ray projector is set substantially perpendicularly to the surface of a heart in the map image.

10. The X-ray diagnostic apparatus according to claim 7, wherein the movement control means includes an accelerator-type foot switch which is configured to control, in accordance with a step amount thereof, the movement amount of the imaging system moving means.

11. An X-ray diagnostic apparatus comprising:

imaging means including an X-ray application unit which applies X-rays to a subject and an X-ray detection unit which detects the X-rays applied from the X-ray application unit to pick up a medical image;

position calculating means for obtaining imaging positions for the subject on the basis of blood vessel numbers anatomically allocated to organs inside the subject;

a storage unit which stores the imaging position;

imaging system moving means for movably supporting the imaging means to capture the imaging position in an imaging field; and movement control means for moving the imaging system moving means to successively move the imaging position along the imaging positions obtained by the position calculating means.

12. The X-ray diagnostic apparatus according to claim 11, wherein the imaging system moving means includes a substantially C-shaped arm which supports the X-ray application unit and the X-ray detection unit, a support mechanism which rotatably supports the substantially C-shaped arm, and a rotational driving unit which drives the rotation of the substantially C-shaped arm; and the movement control means includes an operation unit provided with buttons corresponding to the blood vessel numbers, the movement control means obtaining a rotation angle of the substantially C-shaped arm at the imaging position on the basis of the blood vessel number allocated to the pressed button, and controlling the rotation angle of the substantially C-shaped arm at each position accordingly.

13. The X-ray diagnostic apparatus according to claim 12, wherein when a plurality of buttons are pressed, the movement control means sets, as imaging directions, center-of-gravity angles of imaging angles for blood vessels corresponding to the blood vessel numbers allocated to the respective buttons.

14. The X-ray diagnostic apparatus according to claim 13, wherein the imaging direction is the direction of a straight line connecting the blood vessel to the center of the organ to which the blood vessel belongs.

15. The X-ray diagnostic apparatus according to claim 12, wherein when a plurality of buttons are successively pressed, the movement control means designates a path of the imaging means to sequentially satisfy imaging angles for blood vessels corresponding to the blood vessel numbers allocated to the respective buttons.

16. The X-ray diagnostic apparatus according to claim 15, wherein the imaging direction is the direction of a straight line connecting the blood vessel to the center of the organ to which the blood vessel belongs.

* * * * *